United States Patent [19]
Park et al.

[11] Patent Number: 5,868,868
[45] Date of Patent: *Feb. 9, 1999

[54] PEG-MODIFIED PROTEASES AND METHODS OF USE IN CONTACT LENS CLEANING

[75] Inventors: Joonsup Park; Ronald P. Quintana; Bor-shyue Hong; Bahram Asgharian, all of Arlington, Tex.

[73] Assignee: Alcon Laboratories, Inc., Fort Worth, Tex.

[*] Notice: The term of this patent shall not extend beyond the expiration date of Pat. No. 5,605,661.

[21] Appl. No.: 820,186

[22] Filed: Mar. 19, 1997

Related U.S. Application Data

[63] Continuation of Ser. No. 491,754, Jun. 19, 1995, abandoned.

[51] Int. Cl.$^6$ ............................ C11D 3/386; B08B 3/08
[52] U.S. Cl. ........................... 134/42; 510/392; 510/530; 510/113; 510/114; 435/187; 435/188; 435/219; 435/220; 424/94.3
[58] Field of Search ..................... 435/187, 188, 435/219–225; 510/392, 530, 113, 114; 424/94.3; 134/42

[56] References Cited

U.S. PATENT DOCUMENTS

| | | | |
|---|---|---|---|
| Re. 32,672 | 5/1988 | Huth et al. | 252/95 |
| 3,607,653 | 9/1971 | Ziffer et al. | 195/63 R |
| 3,873,696 | 3/1975 | Randeri et al. | 424/153 |
| 3,910,296 | 10/1975 | Karageozian et al. | 134/2 |
| 3,931,319 | 1/1976 | Green et al. | 260/567.6 P |
| 4,002,531 | 1/1977 | Royer | 195/68 |
| 4,026,945 | 5/1977 | Green et al. | 260/567.6 P |
| 4,179,337 | 12/1979 | Davis et al. | 435/181 |
| 4,407,791 | 10/1983 | Stark | 424/80 |
| 4,414,127 | 11/1983 | Fu | 252/95 |
| 4,525,346 | 6/1985 | Stark | 424/80 |
| 4,614,549 | 9/1986 | Ogunbiyi et al. | 134/19 |
| 4,615,882 | 10/1986 | Stockel | 424/80 |
| 4,670,417 | 6/1987 | Iwasaki et al. | 514/6 |
| 4,758,595 | 7/1988 | Ogunbiyi et al. | 514/635 |
| 4,836,986 | 6/1989 | Ogunbiyi et al. | 422/28 |
| 5,096,607 | 3/1992 | Mowrey-McKee et al. | 252/106 |
| 5,122,614 | 6/1992 | Zalipsky | 548/520 |
| 5,234,903 | 8/1993 | Nho et al. | 514/6 |
| 5,298,410 | 3/1994 | Phillips et al. | 435/188 |
| 5,324,844 | 6/1994 | Zalipsky | 548/520 |
| 5,334,832 | 8/1994 | Phillips et al. | 424/94.3 |
| 5,356,555 | 10/1994 | Huth et al. | 252/106 |
| 5,389,381 | 2/1995 | Phillips et al. | 424/94.3 |
| 5,529,915 | 6/1996 | Phillips et al. | 435/188 |
| 5,605,661 | 2/1997 | Asgharian et al. | 422/200 |
| 5,661,020 | 8/1997 | Snow et al. | 435/188 |
| 5,672,213 | 9/1997 | Asgharian et al. | 134/42 |
| 5,672,231 | 9/1997 | Asgharian et al. | 1347/42 |

FOREIGN PATENT DOCUMENTS

| | | |
|---|---|---|
| 1 150 907 | 8/1983 | Canada . |
| 0 456 467 A2 | 11/1991 | Canada . |
| 0 584 876 A2 | 3/1994 | European Pat. Off. . |
| 47-16793 | 5/1972 | Japan . |
| 48-16627 | 5/1973 | Japan . |
| 57-24526 | 5/1982 | Japan . |

OTHER PUBLICATIONS

Lo, J.; Silverman, H.; and Korb, D.; "Studies on cleaning solutions for contact lenses", *Journal of the American Optometric Association,* vol. 40, pp. 1106–1109 (1969).

Abuchowski, A., et al., "Cancer Therapy With Chemically Modified Enzymes. I. Antitumor Prooperties Of Polyethylene Glycol–Asparaginase Conjugates", *Cancer Biochemistry and Biophysics,* vol. 7, No. 1, pp. 175–186 (1984).

Royer, G., et al., "Peptide Synthesis in Water and the Use of Immobilized Carboxypeptidase Y for Deprotection", *Journal of the American Chemical Society,* vol 101, No. 12, pp. 3394–3396 (1979).

Fuke, I., et al.; "Synthesis of poly(ethylene glycol) derivatives with different branchings and their use for protein modification", *Journal of Controlled Release,* vol. 30, pp. 27–34 (1994).

Khan, S., et al., "Polyethylene glycol–modified subtilisin forms microparticulate suspensions in organic solvents", *Enzyme Microb. Technol.,* vo. 14, pp. 96–100 (1992).

Shearwater Polymers brochure, "Functionalized Biocompatible Polymers For Research, Polyethylene Glycol Derivatives", Huntsville, AI, pp. 1–24.

*Primary Examiner*—Kery Fries
*Attorney, Agent, or Firm*—Michael C. Mayo

[57] ABSTRACT

The invention discloses PEG-modified proteases, compositions containing these modified enzymes, and methods for using them to clean contact lenses. The methods of the present invention are also directed to the simultaneous cleaning and disinfecting of contact lenses, when compositions of the present invention are combined with a suitable disinfectant.

17 Claims, No Drawings

PEG-MODIFIED PROTEASES AND METHODS OF USE IN CONTACT LENS CLEANING

This application is a continuation of application Ser. No. 08/491,754, filed Jun. 19, 1995, now abandoned.

The present invention relates to alkoxy-polyoxyethylene glycol (Al-PEG)-modified enzymes. In particular, the present invention is directed to Al-PEG-modified proteases for use in contact lens cleaning. The invention also relates to methods of simultaneously cleaning and disinfecting contact lenses.

BACKGROUND OF THE INVENTION

Various compositions and methods for cleaning contact lenses have been described in the patent and scientific literature. Some of these methods have employed compositions containing surfactants or enzymes to facilitate the cleaning of lenses. The use of enzymes, particularly proteases, to clean contact lenses has been described in the patent and scientific literature. The first discussion of the use of proteolytic enzymes to clean contact lenses was in an article by Lo, et al. in the *Journal of The American Optometric Association*, volume 40, pages 1106–1109 (1969). Methods of removing protein deposits from contact lenses by means of proteolytic enzymes have been described in many publications since the initial article by Lo, et al., including U.S. Pat. No. 3,910,296 (Karageozian, et al.)

Numerous compositions and methods of use for disinfecting contact lenses have also been described. Those methods may be generally characterized as involving the use of heat and/or chemical agents. Representative chemical agents for this purpose include organic antimicrobials such as benzalkonium chloride and chlorhexidine, and inorganic antimicrobials such as hydrogen peroxide and peroxide-generating compounds. U.S. Pat. Nos. 4,407,791 and 4,525,346 (Stark) describe the use of polymeric quaternary ammonium compounds to disinfect contact lenses and to preserve contact lens care products. U.S. Pat. Nos. 4,758,595 and 4,836,986 (Ogunbiyi) describe the use of polymeric biguanides for the same purpose.

Various methods for cleaning and disinfecting contact lenses at the same time have been proposed. Such methods are described in U.S. Pat. Nos. 3,873,696 (Randeri, et al.) and 4,414,127 (Fu), for example. A representative method of simultaneously cleaning and disinfecting contact lenses involving the use of proteolytic enzymes to remove protein deposits and a chemical disinfectant (monomeric quaternary ammonium compounds) is described in Japanese Patent Publication 57-24526 (Boghosian, et al.). The combined use of a biguanide (i.e., chlorhexidine) and enzymes to simultaneously clean and disinfect contact lenses is described in Canadian Patent No. 1,150,907 (Ludwig). Methods involving the combined use of dissolved proteolytic enzymes to clean and heat to disinfect are described in U.S. Pat. No. 4,614,549 (Ogunbiyi). The combined use of proteolytic enzymes and polymeric biguanides or polymeric quaternary ammonium compounds is described in copending, and commonly assigned U.S. patent application Ser. No. 08/156,043 and in corresponding European Patent Application Publication No. 0 456 467 A2. Finally, a method involving the combined use of proteolytic enzymes in tablet form and a biguanide disinfectant is described in U.S. Pat. No. 5,356,555 (Huth).

Although the use of these enzymatic systems provides effective cleaning, a number of problems associated with their use exist. One problem is that residual amounts of the enzyme can bind to the contact lens. This binding can lead to less clarity of vision when using the lens. It can also lead to ocular irritation and immunogenicity, due to the eye's sensitization to the foreign protein. Consequently, the use of enzyme cleaning is generally limited to a once-per-week regimen. As a result, daily supplemental cleaning, which involves the rubbing of the lens with a surfactant, is necessary to clean the lens satisfactorily during the interim period between the weekly enzymatic cleanings. Thus, the contact lens user is burdened by the purchase of two separate cleaners and the employment of them separately in order to effectively clean his lenses. Therefore, although enzyme cleaning systems provide effective cleaning, they have not been fully exploited as a once-per-day regimen for the optimal cleaning and convenience they would otherwise provide. The modification of the enzyme to hinder its binding to the lens would reduce ocular irritation and immunogenicity, improve visual clarity, and therefore enable a more regular use of the enzyme for cleaning contact lenses.

Another problem in current enzyme cleaning which limits it to once-per-week usage is the cumbersome procedure of using tablets containing the enzyme. In order to use such compositions, a separate packet containing a tablet must be opened, the tablet must be placed in a separate vial containing a solution, and the tablet must be dissolved in order to release the enzyme into the solution. This practice is usually performed only once-per-week due to its cumbersome and tedious procedure. The use of enzyme tablets has been necessary, however, as liquid enzyme compositions formulated in the past have been inherently unstable. Therefore, the modification of the enzyme to improve its stability profile, especially for use in newly disclosed, improved liquid compositions, is of great interest.

The covalent linking of proteins with polyethylene glycol (PEG), to yield a polyoxyethylene-protein product, is disclosed by U.S. Pat. No. 4,179,337 (Davis et al.). A variety of publications and patents have described numerous types of PEG-modified proteins and methods of preparation. Davis et al., above, discloses PEG-modified or polypropylene glycol-modified, non-immunogenic polypeptides for use in the circulatory system of the human body. European Patent Application No. 0 584 876 A2 discloses low diol polyalkylene oxide biologically active proteinaceous substances, including a Subtilisin Carlsberg.

The particular covalent linkage is important for the utility desired. Several linkages have been reported, including succinates and carbamates (urethanes), which are disclosed in *Cancer Biochemistry and Biophysics*, volume 7, pages 175–186 (1984) and U.S. Pat. No. 5,234,903 (Nho et al.), respectively. Although the urethane linkage is purported to be an improvement in stability over the succinate linkage, both linkages are esters and are, therefore, susceptible to hydrolytic cleavage. The compounds of the present invention contain a stable ether or amide bond to facilitate a stable covalent linkage of a protease with an Al-PEG moiety.

SUMMARY OF THE INVENTION

The present invention is directed to the provision of stable, non-irritating, non-immunogenic, and low contact lens binding modified-proteases for the cleaning of contact lenses. In particular, these compounds are alkoxy-polyoxyethylene glycol (Al-PEG)-modified proteases, wherein a proteolytic enzyme is linked via an ether or amide bond to an Al-PEG moiety. The present invention is also directed to compositions containing these modified proteases.

The present invention is directed to methods of using the compounds and compositions of the present invention to clean contact lenses. Methods of simultaneously cleaning and disinfecting contact lenses are also contemplated by the present invention.

The present invention improves on current enzyme cleaning protocols for contact lenses. In one aspect of the present invention, the compounds were designed to avoid ocular irritation and/or immunogenicity resulting from frequent contact of the enzyme with ocular tissues. Another advantage of the compounds is that they bind minimally to contact lenses, thus preventing ocular contact and the problems described above.

DETAILED DESCRIPTION OF THE INVENTION

The present invention provides complexes of formula (I):

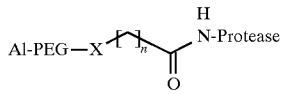
(I)

wherein:

X is O or (C=O)NH;

n is 1 to 10, provided that when X is (C=O)NH, n is 2;

Al-PEG is an alkoxypolyoxyethylene polymer of various size, wherein Al is alkyl, aryl or alkylaryl;

Protease is any enzyme generally characterized as a proteolytic enzyme, wherein the enzyme is linked to an activated Al-PEG moiety at any free amino ($NH_2$) group on the enzyme.

The Al-PEG-proteases which may be utilized in the compositions and methods of the present invention include all enzymes which: (1) are useful in removing deposits from contact lenses; (2) cause, at most, only minor ocular irritation in the event a small amount of enzyme contacts the eye as a result of inadequate rinsing of a contact lens; (3) are relatively chemically stable and effective in the presence of the antimicrobial agents described below; and (4) do not adversely affect the physical or chemical properties of the lens being treated. For purposes of the present specification, enzymes which satisfy the foregoing requirements are referred to as being "ophthalmically acceptable."

Examples of suitable proteolytic enzymes for Al-PEG modification include, but are not limited to: subtilisin, typsin, collagenase, keratinase, carboxylase, aminopeptidase, Aspergillo peptidase, pronase E (from *S. griseus*) and dispase (from *Bacillus, polymyxa*) and mixtures thereof.

The proteolytic enzymes used herein must have at least a partial capability to hydrolyze peptide-amide bonds which reduces the proteinaceous material to smaller watersoluble subunits. As used herein, a "proteolytic enzyme" or "protease" is any enzyme capable of hydrolyzing a peptide-amide bond. The proteolytic enzymes of the present invention include proteases derived from various sources including animal, plant, fungal and microbial sources.

The microbial proteolytic enzymes of the present invention are derived from such groups as the *Bacillus, Streptomyces,* and *Aspergillus* microorganisms. Of this group of enzymes, the most preferred are the Bacillus derived alkaline proteases generically called "subtilisin" enzymes.

The identification, separation and purification of enzymes have been disclosed in the art. Many identification and isolation techniques exist in the general scientific literature for the isolation of enzymes. The enzymes contemplated by this invention can be readily obtained by known techniques from plant, animal or microbial sources.

With the advent of recombinant DNA techniques, it is anticipated that new sources and types of stable enzymes will become available. Such enzymes should be considered to fall within the scope of this invention so long as they meet the criteria for stability and activity set forth herein.

Subtilisin is a preferred enzyme for use in the present invention. Subtilisin is derived from *Bacillus* bacteria and is commercially available from various commercial sources including Novo Industries (Bagsvaerd, Denmark), Fluka Biochemika (Buchs, Germany) and Boehringer Mannheim (Indianapolis, Ind., U.S.A).

Polyethylene glycols (PEG) are a general class of polyetheralcohols according to formula (II):

(II)

wherein, n is 4 to 1000.

PEGs are commercially available from numerous sources including Aldrich (Milwaukee, Wis., U.S.A.) and TCI America (Portland, Oreg., U.S.A.). PEGs are generally a heterogenous mixture of formula (II), and are named for their average molecular weight. For example, PEG 600 is a mixture containing PEGs with n values between 12.5 and 13.9, and having a range of molecular weights from 570 to 630 daltons. PEGs exist in the form of a clear, viscous liquid or a white solid, depending on the molecular weight, which dissolves in water forming transparent solutions.

Alkoxypolyoxyethylene monoalcohols (Al-PEG-OH) are a general class of monoalkoxylated PEGs, also described as polyethermonoalcohols, according to formula (III):

(III)

wherein, n is 4 to 1000; and Z is an alkyl chain, aryl group or an alkyaryl chain.

The compounds of formula (III) are directly analogous to those of formula (II). The compounds of (III) can also be derived from those of (II), by alkylating one of the hydroxy groups of (II). Therefore, the same nomenclature used to describe PEGs can also apply to Al-PEG-OHs. Al-PEG-OHs are activated in the present synthesis below, and lose their hydroxy group forming ether or amides when bonded to the protease. As such Al-PEG-OHs become Al-PEGs of the formula (IV):

(IV)

Al-PEG-OHs are commercially available from Shearwater Polymers (Huntsville, Ala., U.S.A.) and TCI America (Portland, Oreg., U.S.A.). Although Al-PEG-OHs are similar to PEG-OHs, only Al-PEG-OHs are used in the present invention. Al-PEG-OHs are monoalcohols in contrast to the diols of PEGs. The use of the monoalcohol allows for only a single covalent linkage between one Al-PEG and a free amino site on the enzyme. Therefore, the use of Al-PEG-OHs avoids the crosslinking that would result if PEGs were employed. This is significant, as cross-linked aggregates can precipitate and also limit the activity of the modified enzyme.

The covalent linkage of various Al-PEGs to proteases are contemplated by the present invention. For example the use of Al-PEG-2000 would result in the heterogenous mixture of Al-PEG-proteases containing Al-PEG chains of an average molecular weight of 2000 daltons. An Al-PEG wherein Z of formula (IV) is methyl, is known as "Me-PEG." Me-PEG-2000 is a preferred Al-PEG moiety of the present invention, and Me-PEG-5000 is most preferred. Me-PEG-subtilisins are a preferred complex of the present invention, and Me-PEG-5000-subtilisin is the most preferred enzyme complex.

The Al-PEG-proteases of the present invention are synthesized by Schemes 1 and 2, below, for methylether and amide linkages, respectively. Other ether linkages can be prepared by methods analogous to Scheme 1. For purposes of illustration, Me-PEG is used to demonstrate these two routes of synthesis. Other Al-PEGs may be used in place of Me-PEG.

corresponding carboxymethyl derivative (ii). N-hydroxysuccinimide/dicyclohexylcarbodiimide (DCC) is then reacted with (ii) to form the activated succinimidyl derivative (iii). The protease is then reacted with (iii) yielding the Me-PEG-protease complex (iv) of the present invention.

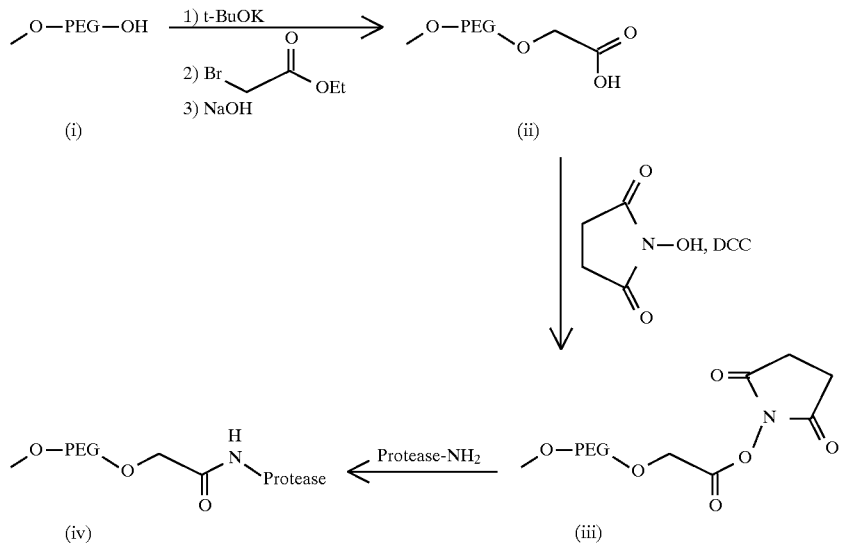

In Scheme 1, methoxy-PEG-OH (Me-PEG-OH) (i) is alkoxylated with potassium t-butoxide, reacted with ethyl bromoacetate and then treated with base, resulting in the

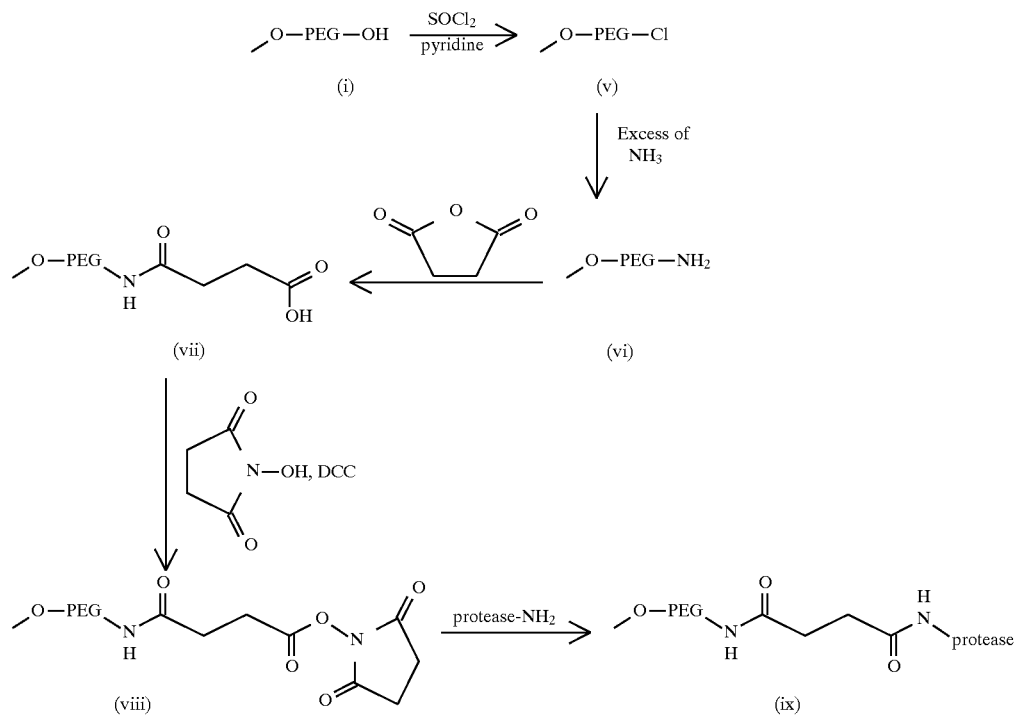

In Scheme 2, Me-PEG-OH (i) is reacted with thionylchloride in the presence of pyridine to give Me-PEG-chloro (v). The product (v) is reacted with excess ammonia to yield Me-PEG-amino (vi). The amide product (vii) is prepared by reacting (vi) with succinic anhydride. The product (vii) is then reacted with N-hydroxysuccinimide/dicyclohexylcarbodiimide (DCC) to give the activated Me-PEG (viii). The product (viii) is then reacted with a protease yielding the final Me-PEG-protease (ix).

Compounds of the present invention are further illustrated by the following synthesis examples:

EXAMPLE 1

Preparation of Me-PEG-5000-Subtilisin

A: Carboxymethylation of Me-PEG-5,000

The process of Royer (*Journal of the American Chemical Society*, volume 101, pages 3394–96 (1979)) and Fuke (*Journal of Controlled Release*, volume 30, pages 27–34 (1994)) was generally followed. In brief, 50.0 grams (g) (0.010 moles (mol)) of poly(ethylene glycol) methyl ether (Me-PEG-5000) and about 100 milliliters (mL) of toluene were added to a 1,000 mL round-bottom flask. The contents were concentrated by rotary evaporation to remove residual moisture (two times), and the residue stirred under high vacuum at 80° C. for several hours. 400 mL of t-butanol, which had been distilled over calcium hydride, was added to the dried Me-PEG-5000, and the mixture was redissolved at 60° C. until all material was dissolved. The solution was allowed to cool to about 45° C. and 46.00 g (0.41 mol) of potassium t-butoxide, which had been dried overnight under high vacuum in the presence of $P_2O_5$, was added. After all of the t-butoxide was dissolved in solution, 60.24 g (0.36 mol) of ethyl bromoacetate was added dropwise through an addition funnel to the stirred solution, at 40° C., then stirred at this temperature for 12 hours. Most of the solvent was removed by rotary evaporation and the residue was redissolved in water. An aqueous solution of 28.25 g (0.71 mol) of sodium hydroxide was added and the solution was stirred at room temperature for two hours. This solution was cooled in an ice bath and acidified to about pH 0–1, by the addition of concentrated HCl (70 mL). The acidic solution was extracted with chloroform (6 times with 100 mL each) and the combined extracts dried over $MgSO_4$. The filtrate was concentrated and precipitated with ether, and then filtered. The precipitate was redissolved in a small amount of chloroform and reprecipitated with ether and filtered. The precipitate was dried to afford 47.0 g (94%) of a white powder, corresponding to the Me-PEG-5000 carboxymethylated acid. NMR was used to monitor the reaction progress and to characterize the final product by comparing the integration of the peaks at 3.35 ppm and 4.12 ppm.

B: Preparation of the activated ester of Me-PEG-5,000 carboxymethylated acid:

20.0 grams of dried (over toluene) Me-PEG-5000 carboxymethylated acid was reacted with 1.61 g of N-hydroxysuccinimide and 2.9 g of dicyclohexylcarbodinide (DCC) at 25°–30° C. in dimethylformamide (100 ml), for 4 hours. The reaction mixture was then filtered directly into ethyl ether to precipitate the product. The precipitate was dissolved in chloroform (50 ml) and precipitated again with ethyl ether to afford 19.5 g (97.5%) of a crystalline product, the activated ester of Me-PEG-5000. NMR spectra confirmed the structure of the final product by comparison of the integration of the end group methyl protons (3.35 ppm) to the methylene protons alpha to the carbonyl group (4.53 ppm), and the four protons in N-hydroxysuccinimide of the product, as well as the disappearance of the resonance at 4.12 ppm in the starting material.

C: Preparation of Me-PEG-5,000-Subtilisin:

In a 3-neck 250 ml flask, 1.35 g (0.05 milimoles (mmol) of Subtilisin A (NovoNordsk, Bagsvaerd, Denmark) in 150 ml borate buffer at 3°–5° C., was reacted with 10 g of polyethylene glycol-5000 monomethylether N-hydroxysuccinimide ester (activated Me-PEG-5000). The pH of the reaction mixture was maintained at pH 8.5 with 1 molar (M) sodium hydroxide. An additional 5 g of the activated Me-PEG-5000 was added every hour until a total of 25 g (5 mmol) had been added. The reaction mixture was then stirred for four more hours. The reaction mixture was then dialyzed in a 12,000–14,000 dalton molecular weight cutoff dialysis tubing for two days. This dialyzed material was then lyophilized to yield 23.94 g (90.9%) of Me-PEG-5000-Subtilisin. Gel electrophoresis and ultraviolet spectroscopy were utilized to characterize and confirm the biochemical and physicochemical properties of the modified product.

EXAMPLE 2

Preparation of Me-PEG-2000-Subtilisin

A: Preparation of Carboxymethylated Me-PEG-2000

The same procedure was followed as described in the synthesis of carboxymethylated Me-PEG-5000 in Example 1A. Briefly, 20 g of Me-PEG-2000, 43 g of potassium t-butoxide, and 32 g of ethyl bromoacetate were used. This resultant product after the reaction and subsequent deesterfication with NaOH, afforded about 20 g of the crystalline product with nearly a 100% yield. The modification efficiency was determined by NMR, as described in Example 1.

B: Activation of the Carboxymethylated Me-PEG-2000:

The dried carboxymethylated Me-PEG-2000, which was dried by distillation over toluene, was activated with N-hydroxysuccinimide (6 g) in the presence of 10.5 g of dicyclohexylcarbodiimide in dimethylformamide. This coupling reaction was run at room temperature for 4 hours and filtered into ethyl ether. The isolated precipitate was dissolved in chloroform and precipitated again with ethyl ether. The reaction product yielded almost a quantitative amount (15 g) of the crystalline product. NMR was employed to confirm the reaction progress, as described in Example 1.

C: Preparation of Me-PEG-2000-Subtilisin:

The same procedure for Example 1C was followed, substituting the activated Me-PEG-2000 for the analogous Me-PEG-5000 as in Example 1B, yielding Me-PEG-2000-Subtilisin.

EXAMPLE 3

Preparation of Me-PEG-550-Subtilisin

A: Preparation of Carboxymethylated Me-PEG-550 and B: Activation of the acid with N-hydroxysuccinimide:

The same procedure as described for Me-PEG-5000 carboxymethylation was followed. Briefly, 10 g of dried (over toluene) Me-PEG-550, 11.8 g of potassium t-butoxide, and 4.4 g of ethyl bromoacetate were reacted as described in Example 1A. The resultant acid (6 g) was activated by reaction with N-hydroxysuccinimide and DCC in ethyl acetate. The reaction mixture was then filtered directly into ethylether to precipitate the product. The precipitate was dissolved in chloroform (50 ml) and precipitated again with ethyl ether to afford 6 g of a crystalline product, the activated ester of Me-PEG-550. NMR spectra confirmed the structure of the final product, as described in Example 1.

C: Preparation of Me-PEG-550-Subtilisin

The same procedure was followed for Example 1C, substituting the Me-PEG-550 activated ester product for the analogous Me-PEG-5000 product, yielding the corresponding Me-PEG-550-subtilisin.

The compositions of the present invention may be either in solid or liquid form. Solid forms usually encompass a compressed tablet wherein various excipients are employed. For example, components such as effervescing agents, stabilizers, buffering agents, chelating and/or sequestering agents, coloring agents, tonicity adjusting agents, surfactants and the like can be employed. In addition, binders, lubricants, carriers, and other excipients normally used in producing tablets may be incorporated into the enzyme tablet when enzyme tablets are employed.

Examples of suitable buffering agents which may be incorporated into an enzyme tablet or working solution include, but are not limited to, alkali metal salts such as potassium or sodium carbonates, acetates, borates, phosphates, citrates and hydroxides, and weak acids such as acetic and boric acids. Preferred buffering agents are alkali metal borates such as sodium or potassium borates. Additionally, other pH adjusting agents may be employed such as inorganic or organic acids and bases. For example, hydrochloric acid, sodium hydroxide, triethanolamine or Tris may be employed in concentrations suitable for ophthalmic uses. Generally, buffering agents are present in amounts from about 0.01 to about 2.5% (w/v) and preferably, from about 0.5 to about 1.5% (w/v), of the working solution.

Effervescing agents are typically employed when the enzyme is provided in solid form. Examples of suitable effervescing agents include, but are not limited to, tartaric or citric acid used in combination with a suitable alkali metal salt such as sodium carbonate.

The tonicity adjusting agent which may be a component of a disinfecting solution and may optionally be incorporated into an enzyme tablet is employed to adjust the osmotic value of the final cleaning and disinfecting solution to more closely resemble that of human tears and to maintain a suitable level for optimum activity by the antimicrobial agent. Typical tonicity adjusting agents are NaCl and KCl.

Suitable surfactants can be either cationic, anionic, nonionic or amphoteric. Preferred surfactants are neutral or nonionic surfactants which may be present in amounts up to 5% (w/v). Examples of suitable surfactants include, but are not limited to, polyethylene glycol ether or esters of fatty acids, polyoxyethylene-polyoxypropylene block copolymers of ethylene diamine (i.e., poloxamine), polyoxypropylene-polyoxyethylene glycol nonionic block polymers (i.e., polaxamers such as Pluronic F-127) and p-isooctylpolyoxyethylene phenol formaldehyde polymers (i..e, Tyloxapol).

Examples of preferred chelating agents include ethylenediaminetetraacetic acid (EDTA) and its salts (disodium) which are normally employed in amounts from about 0.025 to about 2.0% (w/v). Other known chelating (or sequestering agents) can also be employed.

The binders and lubricants for enzyme tableting purposes and other excipients normally used for producing powders, tablets and the like, may be incorporated into enzyme tablet formulations.

A disinfecting agent may optionally be added to the enzyme tablet. Such disinfectants include those described below in the methods of the present invention.

Liquid compositions are preferred Al-PEG-protease compositions of the present invention. Such compositions will be comprised of one or more Al-PEG-proteases of the present invention and a suitable liquid vehicle. As used herein, the term "suitable liquid vehicle" refers to any aqueous or non-aqueous carrier that provides stabilization of the enzyme and preservation of the composition for multiple use dispensing.

Stabilizing agents in aqueous compositions generally include a polyol, such as glycerol, propylene glycol or polyethylene glycol; and an acidic compound such as sodium borate, phenylborate or benzoic acid. Optional ingredients may include a preservative and/or a disinfectant, such as polyquatemium-1; a tonicity adjusting agent, such as NaCl of KCl; a surfactant; and a chelating agent.

The compositions of the present invention are further illustrated by the following examples:

EXAMPLE 4

The following composition represents a preferred enzymatic cleaner tablet:

| Ingredient | mg/50 mg Tablet |
|---|---|
| Al-PEG-5000 subtilisin | 0.5 |
| Citric Acid | 5.95 |
| Sodium Bicarbonate | 13.135 |
| Povidone (K 29–32) | 0.415 |
| Polyethylene Glycol (3350) | 0.75 |
| Compressible Sugar | QS |
| Alcohol | QS* |

*evaporated during processing

The above ingredients are combined and formed into tablets of appropriate size and hardness, according to methods known to those skilled in the art.

This tablet may also be formulated with a seal coating and/or a delayed release coating to provide for a delay in dissolution of up to about 2 hours.

EXAMPLE 5

The following example is a preferred liquid composition of the present invention:

| Ingredient | weight/volume (%) |
|---|---|
| Me-PEG-5000 subtilisin | 6.5 |
| Sodium Borate | 1.0 |
| Glycerol | 50 |
| Polyquaternium-1 | 0.01 |
| Sodium Hydroxide or Hydrochloric acid | QS* |
| Purified Water | QS |

*Quantity sufficient to bring composition to pH 7.5

The methods of the present invention will involve the use of an amount of an Al-PEG protease effective to remove substantially or to reduce significantly deposits of proteins and other materials typically found on human-worn contact lenses. For purposes of the present specification, such an amount is referred to as "an amount effective to clean the lens." The amount of enzyme or enzymes used in particular embodiments of the present invention may vary, depending on various factors, such as the protein content of the complex, the proposed duration of exposure of lenses to the enzymes, the nature of the lens care regimen (e.g., the frequency of lens disinfection and cleaning), the type of lens being treated, and the use of adjunctive cleaning agents (e.g., surfactants). In general, enzymes in the range of 0.001 to 1.0% weight/volume of soaking solution will be used.

The compositions and methods of the present invention may use a disinfectant or disinfecting solution containing an antimicrobial agent. Antimicrobial agents can be oxidative, such as hydrogen peroxide, or non-oxidative polymeric antimicrobial agents which derive their antimicrobial activity through a chemical or physiochemical interaction with the organisms. As used in the present specification, the term "polymeric antimicrobial agent" refers to any nitrogen-containing polymer or co-polymer which has antimicrobial activity. Preferred polymeric antimicrobial agents include: polymeric quaternary ammonium compounds, such as disclosed in U.S. Pat. Nos. 3,931,319 (Green, et al.), 4,026,945 (Green, et al.) and 4,615,882 (Stockel, et al.) and the biguanides, as described below. The entire contents of the foregoing publications are hereby incorporated in the present specification by reference. Other antimicrobial agents suitable in the methods of the present invention include: benzalkonium halides, and biguanides such as salts of alexidine, alexidine free base, salts of chlorhexidine, hexamethylene biguanides and their polymers. The polymeric antimicrobial agents used herein are preferably employed in the absence of mercury-containing compounds such as thimerosal. The salts of alexidine and chlorhexidine can be either organic or inorganic and are typically gluconates, nitrates, acetates, phosphates, sulphates, halides and the like.

Particularly preferred are polymeric quaternary ammonium compounds of the structure:

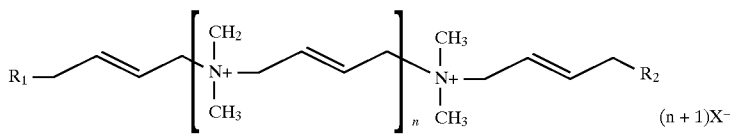

V wherein:
$R_1$ and $R_2$ can be the same or different and are selected from:
$N^+(CH_2CH_2OH)_3X^-$, $N(CH_3)_2$ or $OH$;
X is a pharmaceutically acceptable anion, preferably chloride; and
n=integer from 1 to 50.

The most preferred compounds of this structure is polyquaternium-1, which is also known Onamer M™ (registered trademark of Onyx Chemical Corp.) or as Polyquad® (registered trademark of Alcon Laboratories, Inc.). Polyquaternium-1 is a mixture of the above referenced compounds, wherein X is chloride and $R_1$, $R_2$ and n are as defined above.

The above-described antimicrobial agents are utilized in the compositions and methods of the present invention in an amount effective to eliminate substantially or to reduce significantly the number of viable microorganisms found on contact lenses, in accordance with the requirements of governmental regulatory agencies, such as the U.S. Food and Drug Administration. For purposes of the present specification, that amount is referred to as being "an amount effective to disinfect" or "an antimicrobial effective amount." The amount of antimicrobial agent employed will vary, depending on factors such as the type of lens care regimen in which the method is being utilized. For example, the use of an efficacious daily cleaner in the lens care regimen may substantially reduce the amount of material deposited on the lenses, including microorganisms, and thereby lessen the amount of antimicrobial agent required to disinfect the lenses. The type of lens being treated (e.g., "hard" versus "soft" lenses) may also be a factor. In general, a concentration in the range of about 0.000001% to about 0.01% by weight of one or more of the above-described antimicrobial agents will be employed. The most preferred concentration of the polymeric quaternary ammonium compounds of Formula (V) is about 0.001% by weight.

Oxidative disinfecting agents may also be employed in the methods of the present 5 invention. Such oxidative disinfecting agents include various peroxides which yield active oxygen in solution. Preferred methods will employ hydrogen peroxide in the range of 0.3 to 3.0% to disinfect the lens. Methods utilizing an oxidative disinfecting system are described in U.S. Pat. No. Re. 32,672 (Huth) the entire contents of which, is hereby incorporated in the present specification by reference.

The methods of the present invention will typically involve adding 1 to 2 drops of a liquid enzyme composition or 1 tablet of a solid enzyme composition of the present invention, to 2 to 10 mL of an aqueous solution, placing the soiled lens into the enzyme/disinfectant solution, and soaking the lens for a period of time effective to clean and disinfect the lens. The soiled lens can be placed in the aqueous solution either before or after the addition of the liquid enzyme composition. The aqueous solution may also contain an anti-microbial agent in an amount effective to disinfect the lens. Optionally, the contact lenses are first rubbed with a daily surfactant cleaner prior to immersion in the enzyme/disinfectant solution. The lens will typically be soaked overnight, but shorter or longer durations are contemplated by the methods of the present invention. The methods of the present invention allow the above-described regimen to be performed once per week, but more preferably, every day.

The following examples are presented to illustrate further, various aspects of the present invention, but are not intended to limit the scope of the invention in any respect.

EXAMPLE 6

Methods of the present invention may combine a composition of the present invention with a suitable disinfecting solution. Listed below, is a preferred disinfecting solution:

| Ingredient | weight/volume (%) |
|---|---|
| Polyquaternium-1 | 0.001 + 10% excess |
| Sodium chloride | 0.48 |
| Disodium Edetate | 0.05 |
| Citric acid monohydrate | 0.021 |
| Sodium citrate dihydrate | 0.56 |
| Purified water | QS |

To prepare the above formulation, sodium citrate dihydrate, citric acid monohydrate, disodium edetate, sodium chloride and Polyquaternium-1, in the relative concentrations indicated above, were mixed with purified water and the components allowed to dissolve by stirring with a mixer. The pH was recorded at 6.3 and adjusted to 7.0 with NaOH. Purified water was added to bring the solution to 100%. The solution was stirred and a pH reading of 7.0 was taken. The solution was then filtered into sterile bottles and capped.

The invention in its broader aspects is not limited to the specific details shown and described above. Departures may be made from such details within the scope of the accompanying claims without departing from the principles of the invention and without sacrificing its advantages.

What is claimed is:

1. A modified protease according to formula (I):

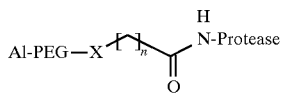
(I)

wherein,

X is O or (C=O)NH;

n is 1 to 10, provided that when X is (C=O)NH, n is 2;

Protease is an enzyme capable of hydrolyzing an amide-peptide bond; and

Al-PEG is a monoalkoxylated polyoxyethylene derivative according to formula (II):

(II)

wherein, m is 2 to 1000; and Z is alkyl, aryl, or alkyaryl.

2. The modified protease according to claim 1, wherein X is O; n is 1 to 2; Al-PEG has a molecular weight of about 5000 daltons; Protease is substilisin; and Z is methyl or ethyl.

3. The modified protease according to claim 1, wherein X is O; n is 1 to 2; Al-PEG has a molecular weight of about 2000 daltons; Protease is substilisin; and Z is methyl or ethyl.

4. The modified protease according to claim 1, wherein X is O; n is 1; Al-PEG has a molecular weight of about 5000 daltons; Protease is substilisin; and Z is methyl.

5. The modified protease according to claim 1, wherein X is (C=O)NH; n is 2; Al-PEG has a molecular weight of about 2000 or 5000 daltons; Protease is subtilisin; and Z is methyl or ethyl.

6. A composition for cleaning a contact lens comprising:

a suitable liquid vehicle; and an ophthalmically acceptable modified protease, in an amount effective to clean the lens, according to formula (I):

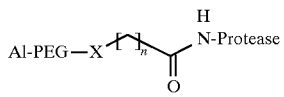
(I)

wherein,

X is O or (C=O)NH;

n is 1 to 10, provided that when X is (C=O)NH, n is 2;

Protease is an enzyme capable of hydrolyzing an amide-peptide bond; and

Al-PEG is a monoalkoxylated polyoxyethylene derivative according to formula (II):

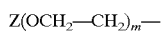
(II)

wherein, m is 2 to 1000; and Z is alkyl, aryl, or alkyaryl.

7. The composition according to claim 6, wherein n is 1 to 2; Al-PEG has a molecular weight of about 5000 daltons; Protease is substilisin; and Z is methyl or ethyl.

8. The composition according to claim 6, wherein n is 1 to 2; Al-PEG has a molecular weight of about 2000; Protease is substilisin; and Z is methyl or ethyl.

9. The composition according to claim 6, wherein n is 1; Al-PEG has a molecular weight of about 5000; Protease is substilisin; and Z is methyl.

10. The composition according to claim 6, wherein X is (C=O)NH; n is 2; Al-PEG has a molecular weight of about 2000 or 5000 daltons; Protease is subtilisin; and Z is methyl or ethyl.

11. A method of cleaning and disinfecting a contact lens comprising a vehicle:

placing the lens in an aqueous solution containing a disinfecting agent in an amount effective to disinfect the lens;

dispersing 1 to 2 drops of a liquid enzyme cleaning composition into said solution to form an aqueous disinfectant/enzyme solution; said composition comprising:

a suitable liquid vehicle;

an ophthalmically acceptable modified protease in an amount effective to clean the lens according to formula (I):

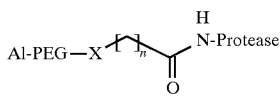
(I)

wherein,

X is O or (C=O)NH;

n is 1 to 10, provided that when X is (C=O)NH, n is 2;

Protease is an enzyme capable of hydrolyzing an amide-peptide bond; and

Al-PEG is a monoalkoxylated polyoxyethylene derivative according to formula (II):

(II)

wherein, m is 2 to 1000; and Z is alkyl, aryl, or alkyaryl;

said composition having a pH of 6–8; and soaking the lens in said aqueous disinfectant/enzyme solution for a period of time sufficient to clean and disinfect the lens.

12. The method according to claim 11, wherein X is O; n is 1 to 2; Al-PEG has a molecular weight of about 5000 daltons; Protease is substilisin; and Z is methyl or ethyl.

13. The method according to claim 11, wherein X is O; n is 1 to 2; Al-PEG has a molecular weight of about 2000 daltons; Protease is substilisin; and Z is methyl or ethyl.

14. The method according to claim 11, wherein X is O; n is 1; Al-PEG has a molecular weight of about 5000 daltons; Protease is substilisin; and Z is methyl.

15. The method according to claim 11, wherein X is (C=O)NH; n is 2; Al-PEG has a molecular weight of about 2000 or 5000 daltons; Protease is subtilisin; and Z is methyl or ethyl.

16. A composition for cleaning a contact lens comprising:

an ophthalmically acceptable modified protease, in an amount effective to clean the lens, according to formula (I):

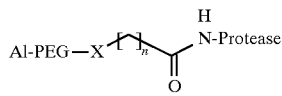

wherein,
X is O or (C=O)NH;
n is 1 to 10, provided that when X is (C=O)NH, n is 2;
Protease is an enzyme capable of hydrolyzing an amide-peptide bond; and
Al-PEG is a monoalkoxylated polyoxyethylene derivative according to formula (II):

 (II)

wherein, m is 2 to 1000; and Z is alky, aryl, or alkyaryl; in a solid carrier therefor.

17. A method of cleaning and disinfecting a contact lens comprising:
placing the lens in an aqueous solution containing a disinfecting agent in an amount effective to disinfect the lens;
dissolving a solid enzyme cleaning composition into said solution, said composition comprising:
an ophthalmically acceptable modified protease in an amount effective to clean the lens according to formula (I):

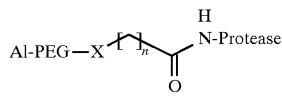

wherein,
X is O or (C=O)NH;
n is 1 to 10, provided that when X is (C=O)NH, n is 2;
Protease is an enzyme capable of hydrolyzing an amide-peptide bond; and
Al-PEG is a monoalkoxylated polyoxyethylene derivative according to formula (II):

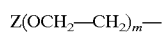 (II)

wherein, m is 2 to 1000; and Z is alkyl, aryl, or alkyaryl; in a solid carrier therefor;
said composition having a pH of 6–8; to form an aqueous disinfectant/enzyme solution; and
soaking the lens in said aqueous disinfectant/enzyme solution for a period of time sufficient to clean and disinfect the lens.

* * * * *